United States Patent [19]

Loher

[11] 4,045,680
[45] Aug. 30, 1977

[54] SHIELDING ARRANGEMENT FOR A ROD SHAPED UV RADIATOR

[76] Inventor: Alois Loher, Talblick 16, D-8451 Haselmuhl, Germany

[21] Appl. No.: 700,732

[22] Filed: June 28, 1976

[30] Foreign Application Priority Data

July 1, 1975 Germany .............................. 2529166

[51] Int. Cl.² .............................................. G01J 1/00
[52] U.S. Cl. ..................................... 250/504; 250/503
[58] Field of Search ............... 250/493, 504, 503, 505, 250/515; 240/46.49 R

[56] References Cited

U.S. PATENT DOCUMENTS

| | | | |
|---|---|---|---|
| 2,151,309 | 3/1939 | Ainsworth | 240/46.49 R |
| 2,359,021 | 9/1944 | Campbell et al. | 250/503 |
| 2,681,061 | 6/1954 | Modell | 250/504 |

Primary Examiner—Alfred E. Smith
Assistant Examiner—B. C. Anderson
Attorney, Agent, or Firm—Kenyon & Kenyon, Reilly, Carr & Chapin

[57] ABSTRACT

A shielding arrangement for a rod shaped UV radiator, particularly for use in making the air in a room germ free which comprises a rod shaped UV radiator and a number of shielding plates which are held parallel to each other at a predetermined spacing. The shielding plates are aperture disks which are disposed horizontally in the room, each having a hole with dimensions such as to at least admit the UV radiator vertically in the direction of its rod axis. The holes of the individual aperture disks are axially lined up with each other. The shielding arrangement is dimensioned such that the UV light can emerge essentially only between respective adjacent aperture disks.

45 Claims, 14 Drawing Figures

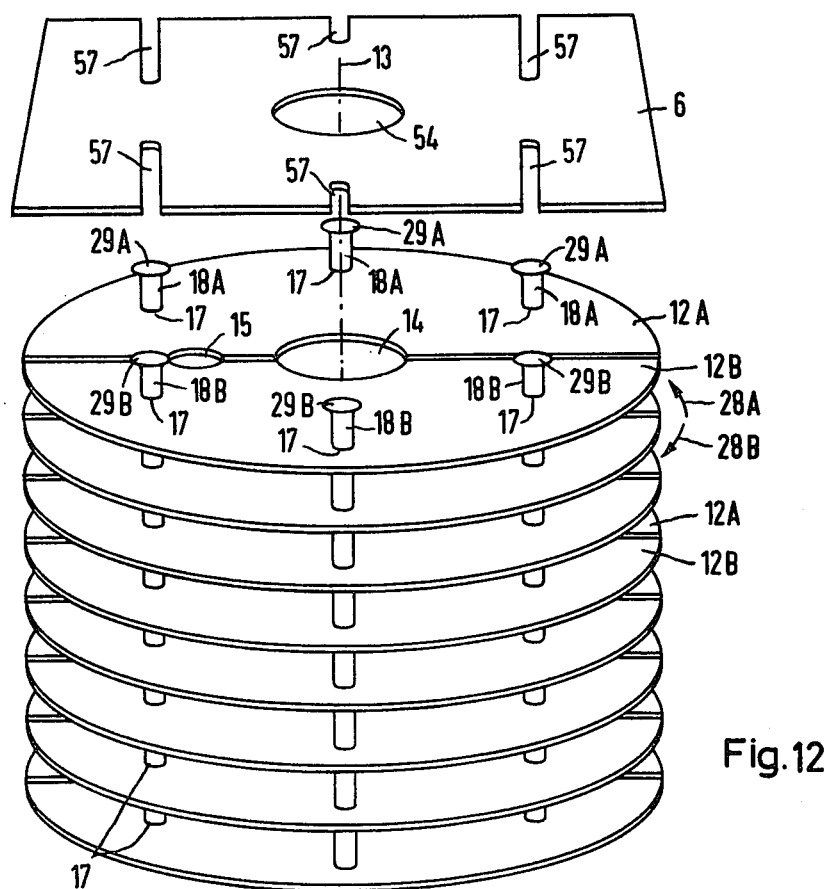
Fig. 12
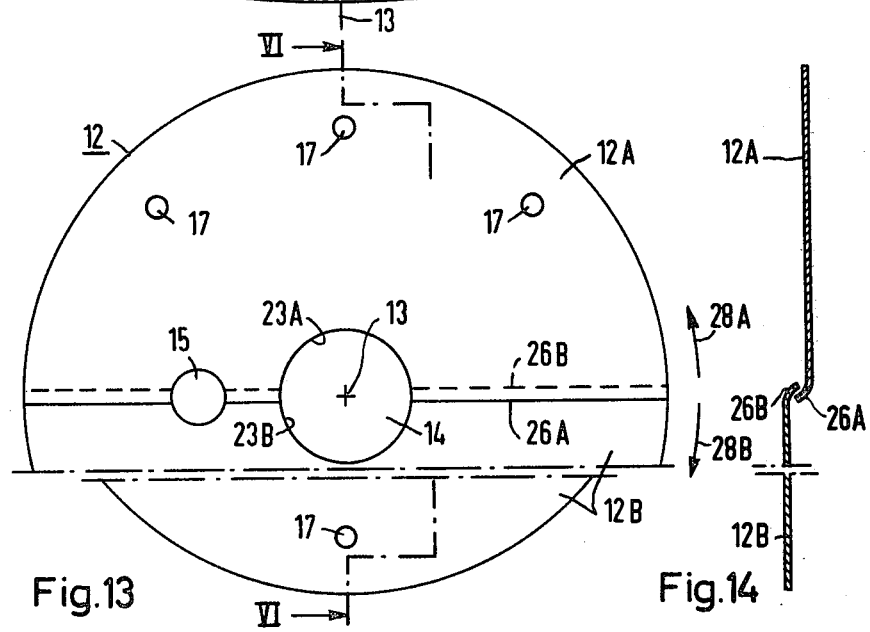
Fig. 13
Fig. 14

SHIELDING ARRANGEMENT FOR A ROD SHAPED UV RADIATOR

BACKGROUND OF THE INVENTION

This invention relates to UV radiators for killing germs in an enclosed space in general and more particularly to a shielding arrangement for a rod shaped UV radiator in which a number of shielding plates are held parallel to each other at predetermined spacings.

In many fields of operation, it is necessary to keep and/or make rooms free of germs. A requirement to disinfect the air and/or the surface of objects exists not only in hospitals and in buildings in the pharmaceutical industry, but also in agricultural operations, particularly in animal breeding and animal farming and in plants which are concerned with the growing of microorganisms and cultrues. In such places it is necessary to keep rooms largely free of germs in order to avoid sickness, growth and output reductions, and to increase the efficiency.

In view of the various types of areas which are disinfected, such areas will hereinafter be referred to as "operations rooms." UV radiators which are mounted in the operations room in question either at the ceiling or at one of the side walls for the purpose of sterilization are known. Such UV radiators are commercially available in rod shaped designs including the necessary starters and ballasts; they are customarily arranged in the room horizontally.

One of the commercially available units has as its major disadvantage that it must be switched off upon the approach of humans in order to avoid radiation exposure. In another unit tiltable reflectors are optionally used, so that the radiation emanating from the UV radiator passes through the room above the eye level of people or animals located in the room in question. Its poor radiation distribution, its poor radiation utilization and the non-uniform irradiation of the room are a disadvantage. With this unit, generally only a small part of the air in the room is irradiated, so that in general, a blower is necessary to obtain uniform distribution of the disinfected air. Such an installation is therefore very expensive.

There is also commercially available an arrangement for a rod shaped UV radiator, in which the rod shaped UV radiator is inserted centrally through a number of ring shaped aperture disks. This is not a shielding arrangement in the proper meaning of the word, i.e., it does not serve to keep the harmful UV radiation away from people or animals in the room; it rather involves a trap for insects which, due to its light emission, attracts flies and other insects and destroys them upon contact. In other words, this arrangement is not intended for disinfecting the room. It emits UV radiation in all directions, i.e., even upward and downward, so that radiation protection is not assured. The purpose of the known aperture disk arrangement is primarily to protect the UV radiator against mechanical damage.

The present invention, on the other hand, addresses the problem of making or keeping, mainly in rooms of normal height, the air and the surface of objects located therein free of germs through the use of a UV radiator. Ideally, it should be possible to operate the UV radiator continuously, and in particular, all day long. Operation even in the presence of people and/or animals without harming them should also be possible. It should further be possible to keep the UV radiator largely free of dust even in rooms with a relatively high dust content, so that even with extended operation of the UV radiator no appreciable drop in the radiation output results.

SUMMARY OF THE INVENTION

It is therefore an object of the present invention to provide a low cost arrangement for a rod shaped UV radiator which can be used in a versatile manner and is easy to install and with which disinfection is possible, utilizing a major part of the emitted UV radiation, and which can continuously be operated without danger to living beings which are in the proximity of the UV radiator.

According to the present invention, this problem is solved by providing aperture disks, each of which has a hole which has dimensions for at least passing the UV radiator in the direction of its rod axis as shielding plates; by aligning the holes of the individual aperture disks axially with respect to each other; and by matching the aperture disks with respect to their hole dimension, their outside dimension, their thickness and their mutual spacing in such a manner that UV light which emanates from a section of this UV radiator located between two adjacent aperture disks when the UV radiator is placed axially through the holes issues with a small aperture angle which is substantially contained between the two adjacent aperture disks but not between other aperture disks.

The invention is based on the premise that in order to solve the stated problem, it is necessary to set up the rod shaped UV radiator vertically, i.e., perpendicular to the ceiling or the floor of the operations room in question, in order to keep the deposit of dust on its radiating surface small, and to equip it additionally with a shielding arrangement which insures that the UV radiation emitted by the UV radiator in all directions does not enter the danger zone of the room which is to be kept free of germs. By the danger zone is meant a zone where exposed parts of an animal or human which can be injured by the radiation will normally be located. Such a danger zone may be situated above the upper end of the rod and/or below the lower end of the rod of the UV radiator. Because of the shielding arrangement, the UV radiator radiates into the operations room substantially only perpendicular to the rod axis. This insures that in any event a zone of air which is situated around the rod shaped UV radiator, is rendered free of germs. The air of this zone is mixed with the air of the danger zone or zones, so that an overall low germ level is brought about in the operations room over an extended period of operation.

The simple presence of aperture disks to a large degree presents dust in appreciable quantities from getting onto the UV radiator. Even so it is advisable to dimension the holes of the aperture disks in the shielding arrangement such as to have diameter somewhat larger than the outside diameter of the rod shaped UV radiator. The clearance between the UV radiator and the edge of the hole makes it possible for dust particles which still strike the UV radiator to trickle down. It should therefore be designed for that purpose. Tests have shown that the UV radiator is kept clean automatically without further measures if the difference between the hole diameter and the outside diameter of the UV radiator is between 1 cm and 4 cm.

In the interest of a symmetrical and simple design, it is particularly advantageous to provide as aperture disks plane or possibly also curved aperture disks and to arrange them concentrically one on top of the other. In particular, each of the aperture disks should be provided with a circular hole.

It is possible to use in the shielding arrangement only shielding disks of the same inside and outside dimensions. Since then only shielding disks of one type are used, such a shielding arrangement can be produced at very low cost. With such a shielding arrangement an upper and a lower danger zone free of radiation is created. However, it is also possible to use aperture disks of the same inside dimension but different outside dimensions. The arrangement is then made so that the aperture disks which follow each other in the connecting line of the holes, have increasing outside dimensions. Such a shielding arrangement is particularly well suited for installation near the ceiling or the floor. It assures greater sterilizing action then a shielding arrangement with shielding disks of the same outside dimension.

Depending on the application, the mutual spacing of all aperture disks can be chosen of the same or of different magnitude. Therefore, a design in which successive aperture disks have increasing mutual spacing is also possible. This design has the advantage that a small number of aperture disks is sufficient.

In the practical construction of the shielding arrangement, care should be taken that the thickness of the aperture disks is substantially less than the outside dimension of these aperture disks. The reason for this is to be found in the saving of material and the desired weight of the shielding arrangement. In addition, only small radiation losses result with thin aperture disks.

Practical tests have shown that, particularly if aperture disks of the same size are used, the aperture angle should be smaller than 20°. It follows that, if circular aperture disks with a circular hole are used, the ratio of the spacing of the aperture disks to their outside radius should be smaller than 0.35 and that the ratio of the inside radius to the outside radius of the aperture disks should be smaller than 0.33.

Any material which is UV-resistant and which is non-deformable at all operating temperatures may be used for the aperture disks. Metal disks, particularly of aluminum, may be used to advantage. Metal disks have a substantial intrinsic stiffness even with small thickness, so that the weight of such a shielding arrangement, which is in itself sufficiently stiff, does not become excessive.

It has been found that UV-resistant plastics are also suitable for the present purposes. Plastic material has the advantage that its specific gravity is low and it is easy to process; however, thicker disks are needed for reasons of stiffness than if metals are used. As a result, the usable radiation output is decreased. Aperture disks of plastic can readily be produced, particularly by injection molding. In order to keep the amount of dust on the aperture disks low, however, antistatic plastic material should be used.

If the shielding arrangement is suspended from the ceiling of an operations room accessible to humans or animals, no undesired stray radiation should be directed downward. Similarly, no undesired stray radiation should be emitted upward of the shielding arrangement if the shielding arrangement stands on the floor. With either kind of installation it is advisable to provide at least the top side or the underside of the aperture disks with a largely reflection-free material in order to prevent emission of stray radiation into the lower or upper danger zone. Through this measure, aperture disks of small dimension suffice. If aperture disks of metal are used, a protective paint or a protective coating of a low-reflection material, particularly of plastic or a commercially available black varnish, can be applied on one side.

The UV-absorbing layer mentioned above may also be a film or an evaporated layer. It is also possible to produce a highly absorbing layer of this by painting or spraying a different material onto the disks.

Outside the danger zone, the reflected radiation does no harm. On the contrary, it is advisable in the interest of good radiation utilization to polish the aperture disks at least on one side, if they are metal disks, or to provide them with a layer which reflects the UV light highly. In particular, the aperture disks may be covered with an aluminum layer since aluminum has good reflective properties in the UV range. Such a highly reflecting layer can be applied to the aperture disks in the form of a film, a vapor-deposited layer, or even by painting or spraying.

One embodiment of the device for holding the disks parallel is designed so that it comprises at least three holding rods which are arranged eccentrically to the rod axis of the UV radiator and which are brought through holes in the aperture disks and through spacers located between respective adjacent aperture disks. In order to prevent the individual aperture disks from shifting, the spacers and the holes for the holding rods arranged in the aperture disks may be made conical.

Particularly if plastic is used as the material for the aperture disks, it is possible to make the aperture disks and the laterally arranged spacers of one piece.

For the practical application of the shielding arrangement it is advisable that one of the holding rods be designed as a tube in which the feed cable for the electrode of the UV radiator facing away from the suspension point is run. Then, the holding rod also assumes the function of a protective device for the feed cable besides holding the assembly together.

It is furthermore advantageous to design the shielding arrangement in such a way that it is made as a structural unit. It can then be installed and removed as a whole, which is advantageous for servicing.

In addition, the soiling of the rod-shaped UV radiator can be reduced further if the shielding arrangement is surrounded on the outside by an electric insect trap known per se. This insect trap consists substantially of a screen which is a high voltage. If circular aperture disks are used this insect trap can be designed in the shape of a cylindrical screen which is arranged concentrically to the aperture disks and the UV radiator. As shown in one embodiment, it is also advantageous if the aperture disks themselves are provided as the electrodes of an electric high-frequency insect trap.

In a practical application, the problem may arise to design the shielding arrangement on the one hand, in such a manner that the UV radiator is easily accessible in its operating position but to also develop it, on the other hand, so that only few parts and few types of parts are required for its assembly.

According to a further embodiment of the present invention, this problem is solved by constructing each aperture disk of a first and a second disk part or subdisk; with the group of all first subdisks detachably joined together with the group of all second subdisks to provide a closed position enclosing the UV radiator in the holes. At least one of the two groups can be disengaged from this closed position, and transferred into a release position which releases the UV radiator.

The basic idea is therefore to subdivide the shielding arrangement formed by the individual aperture disks and the device holding them parallel into two subassemblies which are movable relative to each other. In the closed position, the two subassemblies jointly enclose the UV radiator; this is the normal operating position of the UV radiator, in which living beings which are situated above or below the UV radiator in its vicinity are protected against direct irradiation. In the release position, on the other hand, the subassemblies are detached from each other; the UV radiator is easily accessible, so that it can be cleaned, for instance, or replaced without difficulty. In this release position, the shielding arrangement can also be removed from the UV radiator, which remains stationary. Then, the entire operations room can also be irradited, for instance, in order to bring about sterilization there in a short time.

It is furthermore advisable that the two contact edges of the two subdisks of each aperture disk facing each other be bent toward each other out of the plane of the subdisk, so that they engage each other in the form of a lock in the closed position and overlap in the process. Such a construction provides a high degree of stability of the shielding arrangement. It also assures that no UV radiation can be emitted upward and downward.

A particularly simple and advantageous embodiment with detachable groups of subdisks is furthermore distinguished by the feature that the holding device of at least one of the groups of subdisks consists of tubular holding rods, which are brought through holes in the subdisks perpendicular through the subdisks and are force fitted into these holes. As shown, the holding rods may be provided with enlargements at their one end and may then engage with holes in a base plate.

In the shielding arrangement according to the present invention, it is insured that dust can settle on the UV radiator only in negligible amounts. It is thereby possible to use it even in dusty rooms. The shielding arrangement also insures far reaching freedom from glare downward and/or upward, i.e., into the danger zones. With the shielding arrangement, a large volume of air can be irradiated with little electric power; therefore, one can get along with a small number of UV radiators per room. The shielding arrangement can be produced without great effort at low cost and requires only minimal servicing. It is easy to install and permits easy replacement of wearing parts. It can be used, for instance, in connection with a UV radiator with a wavelength of 254 nm. In addition, one and the same shielding arrangement can be used for a number of commercially available rod shaped UV radiators, so that one can get along with few types of shielding arrangements. Advantageously, the shielding arrangement can also be used for the prevention of odor annoyance without loss of the mentioned advantages.

BRIEF DESCRIPTION OF THE DRAWINGS

FIG. 12 is a perspective view of a shielding arrangement which consists of two subassemblies, in its closed position;

FIG. 13 is a top view of a corresponding aperture disk which consists of two subdisks; and FIG. 14 is a cross-sectional side view of the aperture disks of FIG. 13.

DETAILED DESCRIPTION OF THE INVENTION

Figure 1:
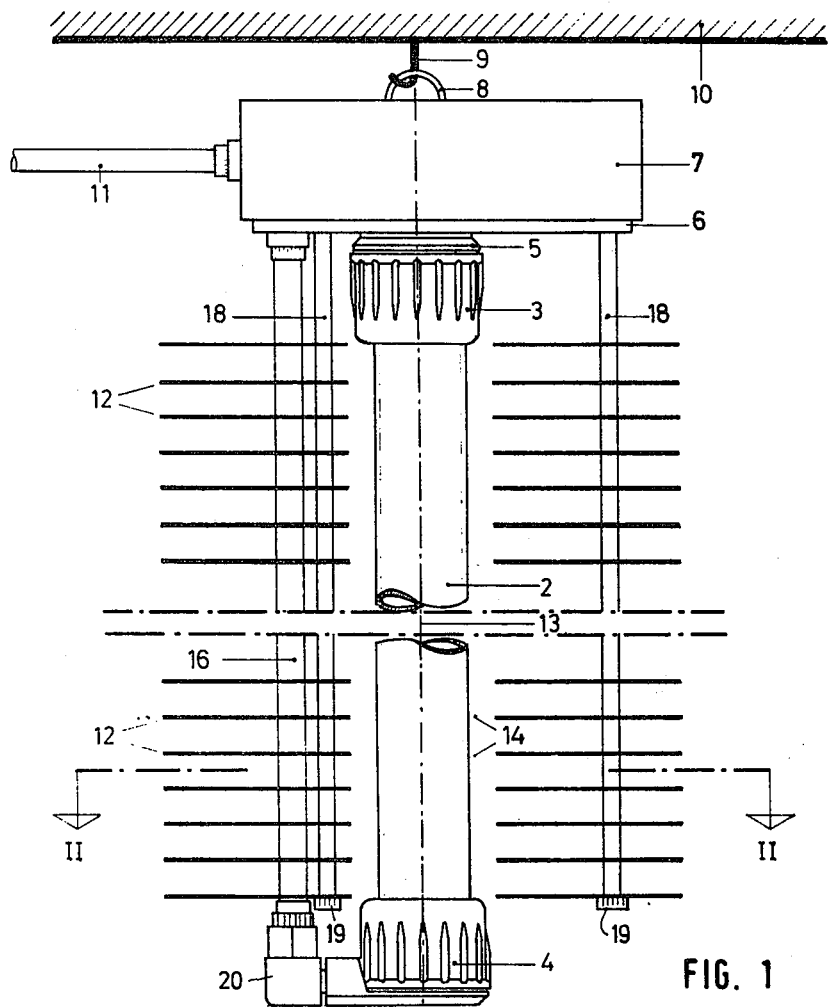
FIG. 1 is a side view of a shielding arrangement for a rod-shaped UV radiator suspended from the ceiling.

FIG. 1 shows a rod shaped UV radiator 2 of circular cross section, which emits UV light, for instance, with a wavelength of 254 nm. It is held detachable in a vertical position by a first and a second socket 3 and 4, respectively. The base body 5, provided with a thread, of the first socket 3 is detachably fastened to a base plate 6. The base plate 6 in turn forms the bottom of a ballast box 7 or is fastened to the bottom of the latter. The ballast box 7 contains a conventional ballast, not shown, a conventional starter, not shown, and the corresponding connecting cables. A first connecting cable, not shown, leads from the interior of the ballast box 7 through the base plate 6 to the base body 5 of the first socket 3.

The ballast box 7 hangs from a hook 9, which is installed in the ceiling 10 of a room which is to be disinfected by means of a suspension device in the form of a loop 8. A chain of several links (not shown) may be provided between the loop 8 and the hook 8 so that the distance of the UV radiator 2 from the ceiling 10 can be adjusted. Held by the structural elements 3 to 9, which forms the suspension device or vertical holding device, the UV radiator 2 hangs freely from the ceiling 10 of the room in a vertical position. The height is adjusted so that the UV radiator 2 is arranged above the eye level of an exposed person or the exposed animal. A supply cable 11, which is connected to the electrical power supply of the work room is laterally run into the ballast box 7.

Figure 2:
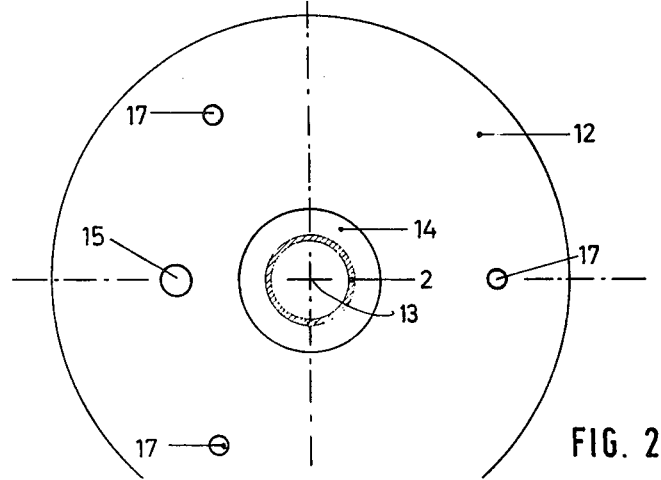
FIG. 2 is a cross section top view of one of the circular shielding disks used in the embodiment of FIG. 1 taken along the section II—II of FIG. 1.
Figure 3:
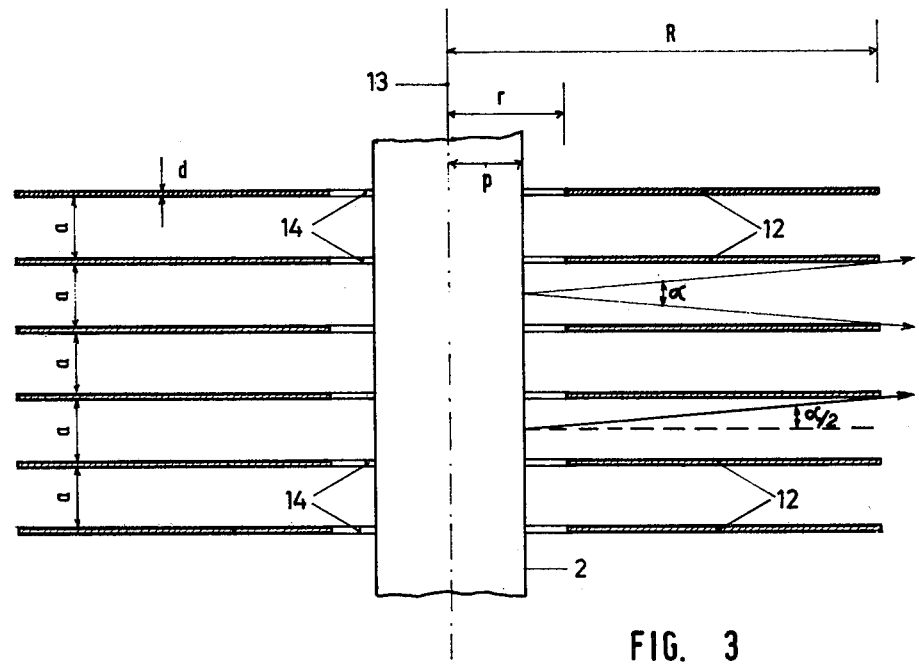
FIG. 3 is a cross-sectional detail drawing of the embodiment of FIG. 1.

In order to shield the downward radiation of the UV radiator 2 to a large extent, a shielding arrangement is provided. This comprises a number of flat aperture disks 12, each of which has a hole 14. In the present embodiment, these are ring shaped aperture disks 12 of equal size, concentrically aligned with the rod axis 13, with a centrally arranged circular hole 14, as can be seen in FIGS. 2 and 3. This form of the aperture disks results in a uniform distribution of the radiation in the work room and is easy to produce. In deviation therefrom, however, it is also possible to use rectangular and oval aperture disk shapes. The shape of the aperture disks can also be fitted to the shape of the work room or to the work station. The dimension of the hole is in the present case 2r and the outside dimension of the aperture disks 12 is 2R. The outside diameter of the UV radiator 2 is 2p (see FIG. 3).

The individual, identical aperture disks 12 are held parallel to each other at some distance in the embodiment of FIG. 1 by a holding device which will be described in detail below. They are aligned concentrically to each other, so that their centrally located holes 14 are also axially aligned with respect to each other. The axis formed by the holes 14 coincides with the rod axis 13 of the UV radiator 2. The mutual spacing $a$ of all aperture disks 12 is the same in this embodiment.

The central holes 14 of the aperture disks 12 are intended and designed for inserting the UV radiator 2 in the direction of its longitudinal axis 13. Since the UV radiator 2 hangs perpendicular to the ceiling 10 because of the vertical mounting device, a substantially horizontal positon is required for the parallel aperture disks 12. This horizontal position is predetermined by a holding device (to be described below in detail). At the same time it insures a central arrangement of the UV radiator 2.

It is evident from FIGS. 1 to 3 that the holes 14 of the aperture disks 12 have a diameter $2r$ somewhat larger than the outside diameter $2p$ of the rod shaped UV radiator 2. Thereby, an approximately equal space with the radial spacing $(r - p)$ is obtained between the surface of the UV radiator 2 and the inner edge of each aperture disk 12 everywhere. This gap width or this radial distance $(r - p)$ is provided on the one hand so that dust which has settled on the surface of the UV radiator 2 and drops off after some time, can fall down through the ring gap without impediment. In this manner, it is insured that even with a shielding arrangement the UV radiator 2 remains clean for a long time, which benefits the light yield and makes cleaning work necessary only after long intervals. On the other hand, the radial spacing $(r - p)$ is also selected so that sufficient cooling of the UV radiator 2 is provided by the rising of the heated air, i.e., an appreciable thermal draft. In practical embodiments, a gap width $(r - p)$ of 0.5 to 2 cm is preferably chosen.

According to FIGS. 1 and 2, the holding device comprises three holding rods 18 which are arranged parallel to each other and eccentric to the rod axis 13. These are brought through corresponding holes 17 in the aperture disks 12. The equidistant aperture disks 12 are fastened to the holding rods in any desired manner, for instance, they may be screwed in place. The three holding rods 18 and the aperture disks held thereon parallel to each other therefore form a column-like unit. This unit is suspended so that the shielding disks 12 are oriented horizontally.

Figure 4:
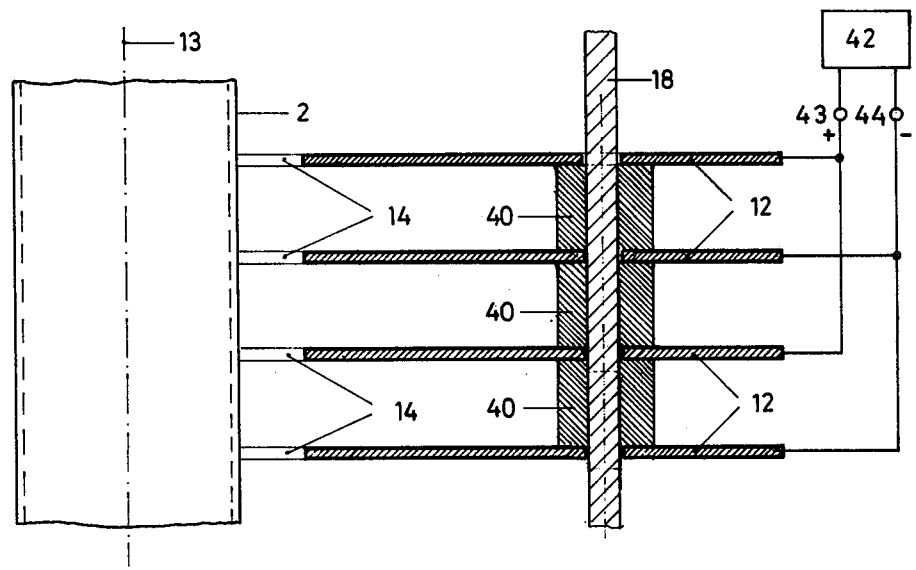
FIG. 4 is a further cross-sectional detail drawing of the embodiment of FIG. 1.

In the embodiment of FIG. 4, the parallel arrangement is achieved by three spacers 40, which are placed between each two adjacent aperture disks 12. These spacers 40, which are of cylindrical shape and are all of equal height, have holes drilled through them and are pushed over the holding rods 18. The spacers 40, the aperture disks 12 and the holding rods 18 are held together by a clamping device. The latter may be, for instance, three resilient plug clamps or, as shown on FIG. 1, three nuts 19 which are screwed on the holding rods 18 at their ends. The upper ends of the holding rods 18 are detachably fastened at the support plate 6.

In principle, one of the holding rods 18 may be designed as a tube, in which an electrical feed cable for the second socket 4 is run. When taking apart the structural unit 12, 18, however, the feed cable would have to be disconnected, for which purpose an electrical plug connection would be required. Therefore, a separate holding tube 16 of metal, e.g., aluminum, is provided which is fastened on the one side to the base plate 6 and on the other side to the connecting piece 20 of the second socket 4. This holding tube 16 contains and protects the feed cable that leads to the electrode facing away from the suspension point of the UV radiator 2. The holding tube 16 is brought through eccentrically arranged holes 15 (see FIG. 2) in the aperture disks 12, in the present case without a joint.

It should further be noted that the hole 14 in the lower aperture disk 12 is covered up by the second socket 4 of the UV radiator 2; this socket is located outside the shielding arrangement.

As can be seen from FIG. 3, four dimensions of the shielding arrangement are of decisive importance for its effectiveness: The outside diameter $2R$ and the inside diameter $2r$ of the ring shaped aperture disks 12, their thickness $d$ and their mutual spacing $a$.

In the interest of low weight for the shielding arrangement and minimum material requirements, the thickness $d$ will be chosen as small as possible, but in any event substantially smaller than the outside diameter $2R$. It will be chosen as small as the material used (metal, plastic) permits without deformation. The thermal stresses in operation also must be taken into consideration. The smaller the thickness $d$, the less will be the absorption at the edges of the disks and the more UV radiation available for the disinfection.

If the thickness $d$ is given, the quantities $R$, $r$ and $a$ must be matched to each other. If shielding disks 12 of equal size are used, the matching is accomplished so that a large portion of the total UV light emitted and substantially only UV light radiated perpendicular to the longitudinal axis 13 can pass freely into the environment of the shielding arrangement. This UV light is to bring about the disinfection of the ambient air without alteration. This is achieved by choosing the quantities $R$, $r$ and $a$ in such a manner that the UV light which emanates from a section of the UV radiator which is located between two adjacent aperture disks 12, 1. can emerge with a small aperture angle $\alpha$ and
2. can emerge substantially only between these two adjacent aperture disks 12, but not between other aperture disks 12.

A small aperture angle $\alpha$ necessitates, as shown by FIG. 3, a small $a/R$ ratio. In practice, it is often sufficient if the aperture angle $\alpha$ is less than 20°. Calculation shows that then the $a/R$ ratio must be smaller than 0.35. An aperture angle $\alpha$ of less than 10° would seem to meet all practical requirements, but also increases the number of the aperture disks 12 required.

The UV light of a section of the UV radiator is prevented from finding a direct path into the environment through the ring gaps formed by the two adjacent aperture disks 12. Calculation shows that this condition is met if the $r/R$ ratio is less than 0.33.

In a practical embodiment $p$ was 1.9 cm, $r = 3.0$ cm, $R = 11.0$ cm and $a = 1.5$ cm. The invention is, of course, not limited to these values.

Similar considerations, incidentally, also apply where in deviation from the embodiment examples of FIGS. 1 to 3, aperture disks of different shape are used. Then, too, substantially horizontal radiation is obtained. It is assured then, too, that the shielding arrangement practically completely shields the radiation emanating from the UV radiator from a person located at the effective UV light distance who has his eyes outside of the height of the UV radiator.

The embodiments of the shielding arrangement explained with the aid of FIGS. 1 to 3 for a vertically arranged UV radiator 2 fully meet the requirements of practice. They also work properly under rough operating conditions. The aperture disks 12 serve not only for shielding, but at the same time protect the UV radiator 2 against damage. The shielding arrangment requires no reflectors of complicated shape that must be mounted separately. Largely, commercially available parts and only slightly different types of parts are used. The shielding arrangement can therefore be produced in quantity production. It is easy to install and wearing parts can readily be replaced. Thus, the installation and servicing costs incurred are low. The UV radiator with the shielding arrangement permits irradiation of a large volume of air with relatively little electric power. Therefore, even a small number of UV radiators per room are sufficient. The design or the present invention makes possible far reaching freedom from glare upward and downward. Dust can settle on the rod shaped UV radiator only in negligible amounts. Therefore, it can also be used in dusty rooms.

It may also be seen from FIG. 4 that the aperture disks 12 of the shielding arrangement themselves can serve as the electrodes of an electric high voltage insect trap. Such an insect trap destroys flies, gnats etc., and protects the UV radiator 2 from being soiled and should be used particularly if the shielding arrangement is employed in animal stables. The aperture disks 12 must then consist at least in part of an electrically highly conductive material, e.g., of aluminum, while the spacers 40 and the holding rods 18 must be made of non-conductive material, e.g., plastic.

According to FIG. 4, a voltage generator 42 is provided which delivers a high voltage at its output terminals 43 and 44. The output terminal 43 is connected to every second aperture disk 12 and the output terminal 44 to the remaining aperture disks 12 in an electrically conducting manner. The approaching insects are destroyed upon contact with a shielding plate 12.

Figure 5:
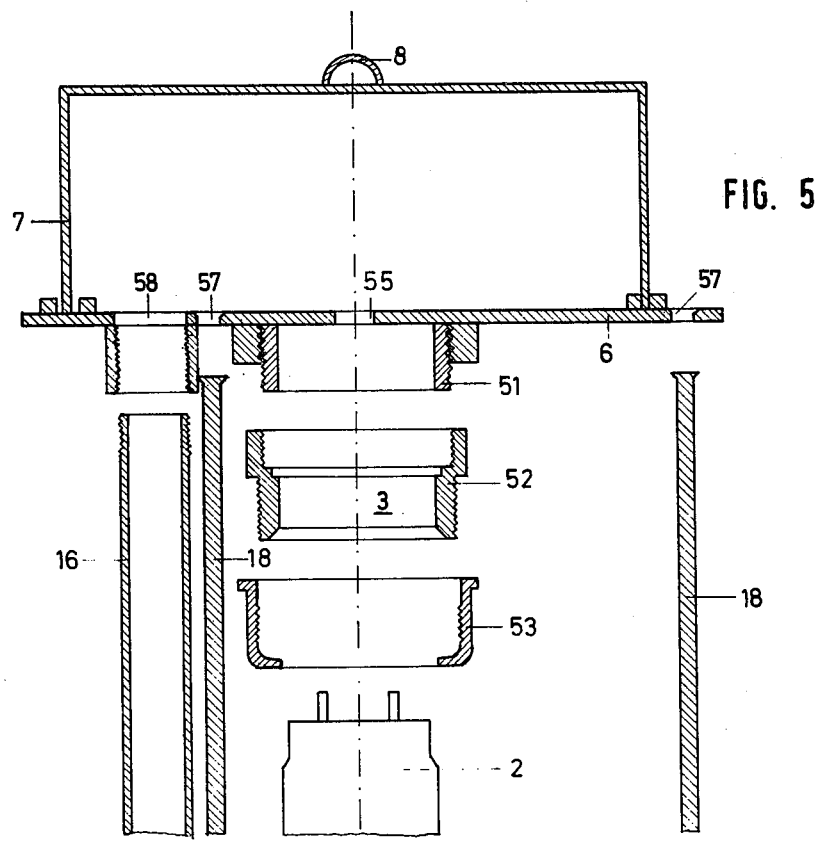
FIG. 5 illustrates an embodiment of means for attachment of the rod shaped UV radiator to a base plate which also supports the shielding arrangement.
Figure 6:
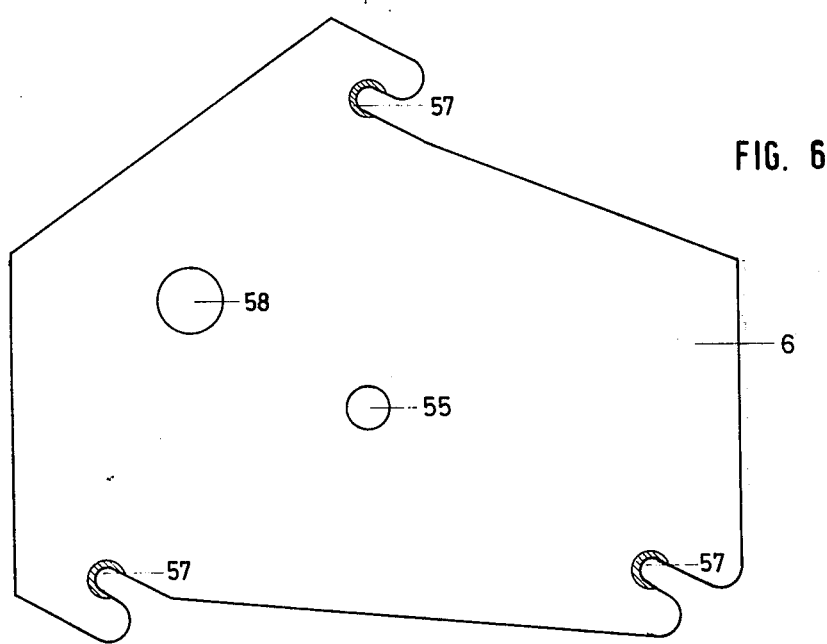
FIG. 6 is a plan view of the base plate of FIG. 5.

In FIGS. 5 and 6, the detachable mechanical fastening of the UV radiator 2, the holding rods 18 and the holding tube 16 to the base plate 6 is shown. Accordingly, the first socket 3 consists of three threaded parts 51, 52 and 53 made of plastic. These are screwed together at the base plate 6, which may likewise consist of plastic. A hole 55 allows the entrance of a connecting wire from the ballast box 7. The holding rods 18 are enlarged at their upper ends. They engage in correspondingly slotted holes 57 in the base plate 7 in the form of a bayonet joint. The unit made up of plates 12 and rods 18 can therefore be detached from the base plate 6 by simple lifting and rotating. For fastening the holding tube 16, a threaded joint is provided. The hole for feeding through the connecting cable for the lower electrode is designated with 58.

Figure 7:
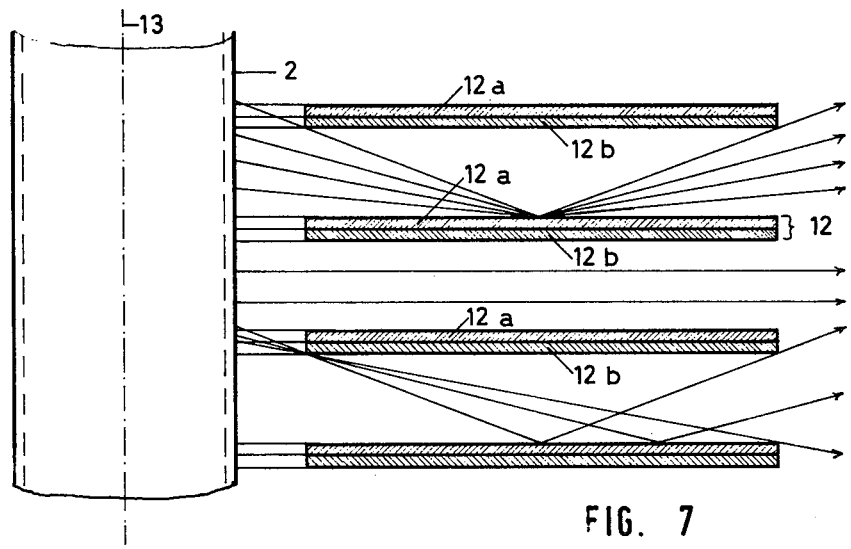
FIG. 7 is a cross sectional view of a shielding arrangement with aperture disks which have different layers.

In FIG. 7 a further shielding arrangement for a rod shaped UV radiator 2 is shown in a partial presentation. Details of the holding device for the aperture disks 12 aligned transversely to the rod axis 13 are omitted for the sake of clarity.

Each aperture disk 12 consists of two disks 12a and 12b closely placed on top of each other. Only one of these two disks 12a and 12b need be stable by itself; the other may be designed as a foil or a thin layer and be cemented or vapor-deposited, sprayed or painted on the inherently stable disk. The inherently stable disk consists preferably of a UV light resistant plastic or aluminum, for weight reasons. Such two layer aperture disks 12 are easy to produce.

According to FIG. 7, each upper disk 12a consists of a material that highly reflects UV light. This may be a polished aluminum plate, which is dimensionally stable and self-supporting at all occurring operating temperatures; but if the lower disk 12b can assume the supporting function, it may also be a thin aluminum foil or also a thin aluminum layer which is applied to the corresponding lower disk 12b, e.g., by cementing or evaporating. UV light incident on the upper disk 12a is predominantly reflected upward because of the good reflection properties of the disks 12a, as indicated by the radiation arrows illustrated. The UV light is therefore not lost by absorption but likewise contributes to the irradiation and disinfection of the room in question. This increases the efficiency and utilization of the shielding arrangement.

According to FIG. 7, each lower disk 12b may consist of a largely reflection free material, i.e., a material which strongly absorbs UV light. Here, too, dimensionally stable and self-supporting plates can be used, or also thin foils or thin layers which are applied by evaporation, brushing or spraying. The UV light incident on these disks 12b is largely absorbed. Mat black varnish can be used as the absorbing material.

The shielding arrangement shown in FIG. 7 thus has a certain directional effect upward. The UV light generated by the UV radiator 2 is radiated into the room either directly with a small aperture angle substantially perpendicular to the rod axis 13 or indirectly, i.e., after reflection, preferably upward. The zone of the room below the lowest aperture disk 12 is not endangered by UV light. The shielding arrangement is therefore particularly well suited for installation at the ceiling of the room in question outside the eye level of those persons and animals in the room in question.

For application of the shielding arrangement near the floor of the room, it is merely necessary to reverse the shielding arrangement, so that now the disk 12a is always at the bottom and the disk 12b at the top. Also in this application, the UV light reflected at the reflecting disks 12a is utilized in an advantageous manner for disinfecting the room without the danger of radiation upward. One and the same design of the shielding arrangement can therefore be used by reversing for different applications, which is considered a particular advantage because of the simplified production requirements and stocking.

It should also be mentioned that the individual aperture disks, if required, can consist also of more than two disks or layers. Thus, it is possible, for instance, to coat an inherently stable plastic or metal aperture disk which is not deformable at operating temperatures, on one side with a UV absorbing layer and on the other side with a UV reflecting layer or similar foil. Such multi-layer aperture disks can likewise be produced inexpensively and easily. The layers applied, particularly sprayed on, on both sides act at the same time as a protective coating, which can be particularly useful for reasons of corrosion protection for application in humid rooms or in rooms with chemically aggressive vapors.

It has already been explained that plastic is suitable as the material for the aperture disks 12 of single layer or multi-layer design. This material, as long as it is not coated with protective layers, must be UV resistant and must be able to withstand the operating temperatures occurring. In order to minimize dust deposits, it is advisable to choose an antistatic plastic material. For reasons of weight, cost and production, a metal such as aluminum is often preferred.

Figure 8:
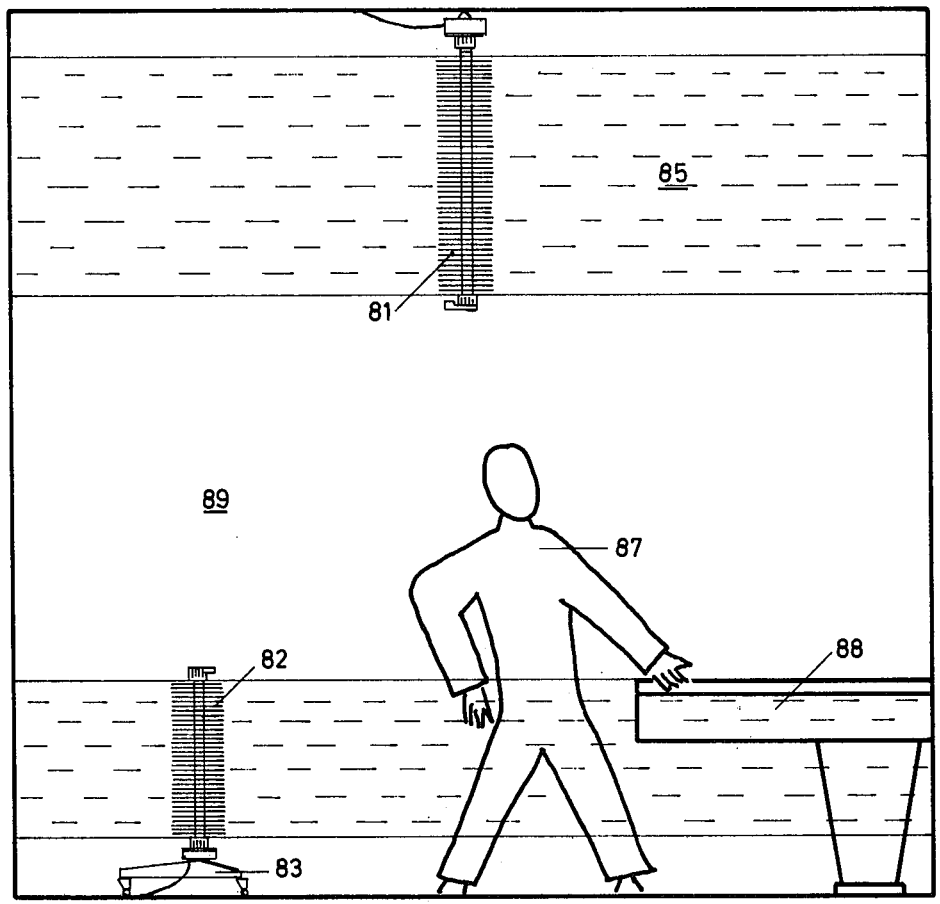
FIG. 8 is a view illustrating the placement of two shielding arrangements in an operations room.

In FIG. 8, first and second shielding arrangements 81 and 82 which include UV radiators of different height are shown in a work room. The first shielding arrangement 81 is suspended from the ceiling of the room which is to be kept free of germs, more specifically, about in its center, and the second shielding arrangement 82 stands on the floor, somewhat to one side, on a stand 83 which is used as the mounting device and can be moved on rollers. It could also be fastened there. Both UV radiators can remain switched on during the work in the room. The position of both UV radiators can be chosen freely. In both shielding arrangements 81, 82, the rod axis of the UV radiator is oriented vertically. Because of the use of parallel aperture disks of equal outside diameter, the UV radiators of both shielding arrangements 81 and 82 radiate their UV radiation into the room substantially only perpendicular to the rod axis. The radiation zones 85 and 86 resulting therefrom are shown by the short lines.

The depth and width of both radiation zones 85 and 86 are chosen so that the head and the upper part of the body of a person 87 in the room, who works, for instance, at a table 88, are always in the radiation-free zone 89 between the radiation zones 85 and 86. It is particularly important that the two UV radiators are arranged outside the range of the eye level of the person 87, which is variable during the work. Because of the chosen heights of the shielding arrangements 81 and 82 with the UV radiators and because of their particular design, it is assured that the person 87 cannot see either UV radiator in any head position, or expressed in the reverse: The UV radiation cannot fall on the eyes of the person 87 and cause damage to them.

In general, the zone are arranged so that other exposed body parts of the person 87, e.g., the hands are not exposed to the UV radiation without protection, or are predominantly in the radiation-free zone 89 during the work. Thus, damage to the skin by the UV radiation is prevented, along with prevention of damage to the eyes.

Thus, it is possible to work in the work room without danger by using the shielding arrangements 81, 82 in spite of the fact that both UV radiators remain continuously switched on and the air is thereby disinfected effectively.

Figure 9:
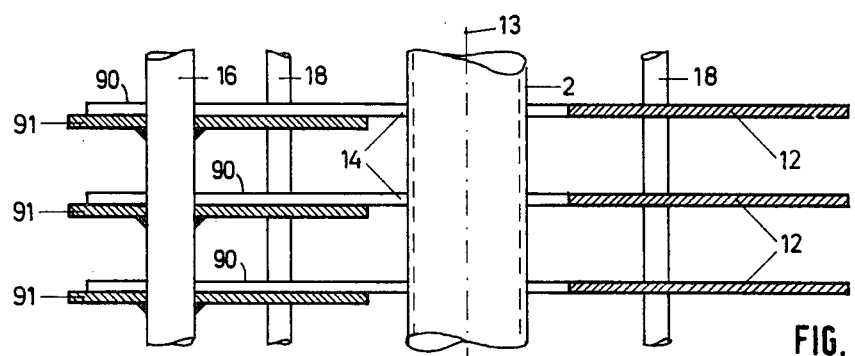
FIG. 9 is a further cross-sectional detail drawing of the embodiment of FIG. 1.
Figure 10:
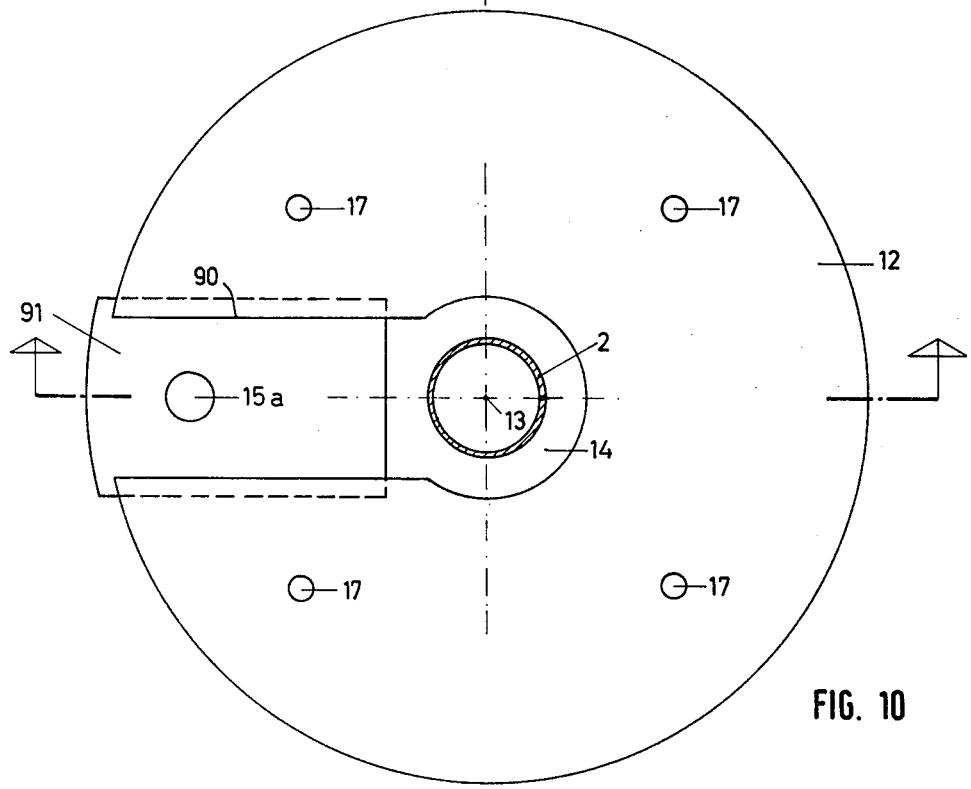
FIG. 10 is a top view onto the shielding disks used in FIG. 9.

It was already emphasized that the aperture disks 12 and the holding rods 18, and also possibly the parts 19 and 40, from a unit. Shown in FIGS. 9 and 10 is such a unit which is designed as a removable and transportable structural unit. With the structural unit removed, servicing, repair and cleaning work is readily possible.

According to FIGS. 9 and 10, each aperture disk 12 has a slot 90 leading to its central hole 14. This slot is designed so that the UV radiator 2 can be led through it from the side. For detaching and removing the structural unit 12, 18 it is therefore merely necessary to take the holding rods 18 from their attachment (of the bayonet type, according to FIGS. 5 and 6) at the base plate 6 and then to move the structural unit 12, 18 laterally to the right.

In order to obtain a stable horizontal position of the aperture disks 12 in spite of the slot 90, holding plates 91 which are fastened at equidistant spacings at the holding tube 16 are additionally provided. In FIG. 9, the attachment to the tube 16 is by the welded seams shown. The holding plates 91, which have holes 15a for receiving the holding tube 16, each serve as a support for one of the aperture disks 12. They are therefore made somewhat wider than the slots 90 in the aperture disks 12.

Figure 11:
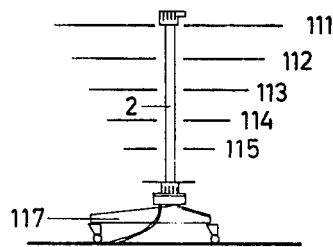
FIG. 11 is a side view of a UV radiator with a shielding arrangement in the form of a truncated cone.

FIG. 11 schematically illustrates a rod shaped UV radiator with a shielding arrangement which is provided for particularly effective sterilization of an air zone near the floor. Deviating from the shielding arrangements in the previous figures, the shielding arrangement shown consists of a number of concentrically arranged aperture disks 111 to 115 with the same inside diameter but different outside diameters. The aperture disks 115 to 111, which follow each other in the connecting line of their central holes, have an outside dimension increasing toward the top. The shielding arrangement thereby acquires the appearance of a truncated cone, as viewed from the side. With this design, the vertically mounted UV radiator 2 is effectively shielded toward the top, while perpendicular to the rod axis and downward, it can radiate unimpeded to a large degree. It is not necessary for this purpose that, if viewed from the side, the two outer boundary lines of the aperture disks 111 to 115 run as straight lines toward each other, as shown in the drawing. In the general case (equidistant spacing of the aperture disks 111 to 115) the boundary lines will be concave with respect to the rod axis or, in an exceptional case, also convex.

In FIG. 11, the UV radiator 2 and the shielding arrangement are disposed on a movable mounting device, specifically, on a stand 117 that can be moved on casters. Thereby, the installation can be adapted very quickly to the different working or operating conditions in the operations room.

In order to get along with a small number of aperture disks 111 to 115, the mutual spacings of the aperture disks 111 to 115 may be made different as an additional measure. It is evident from FIG. 11 that the spacings of the aperture disks 115 to 111 become smaller toward the top. If cylindrical spacers are used, as in FIG. 4, these would therefore have to be made of different lengths. The number of aperture disks 111 to 115 required and the choice of their mutual distances depend greatly on the length of the UV radiator 2 and the size of the room to be irradiated.

With a truncated cone shaped shielding arrangement, better utilization of the UV light emitted and thereby, increased sterilization action can be obtained than with a shielding arrangement of cylindrical appearance (such as, for instance, in FIG. 1) because of the increased aperture angle. A UV radiator with a shielding arrangement which is tapered in the axial direction is therefore particularly well suited for use in the hospital field. Besides the increased sterilization effect, the material savings in the manufacture of the aperture disks 111 to 114 are also a noteworthy advantage. These material savings due to the tapering become particularly important if a large operations room is to be irradiated and/or a long UV radiator is used.

The considerations explained above apply here to that half-aperture angle which points toward the danger zone.

If the shielding arrangement, as shown, is designed as floor equipment, each aperture disk protects the one below it against dust dropping from above and thus, against a reduction of its reflectivity. The shielding arrangement is therefore largely free of maintenance.

The tapered shielding arrangement together with the UV radiator can, of course, also be used as ceiling equipment. In that case, the shielding arrangement shown (without the stand 117) would have to be mounted upside down at the ceiling, so that here again, the aperture disk 111 with the largest dimension is directly adjacent to the danger zone. Such a reversed shielding arrangement makes it possible to irradiate the zone near the ceiling with high intensity, while the zone below is protected from the incidence of UV radiation. Here, too, a low germ level can be maintained in the operations room.

In FIG. 12, a stable base plate 6 which serves to hang a shielding arrangement for a rod shaped UV radiator is shown. The base plate 6 can be fastened by fastening means, not shown, to the ceiling of an operations room, the air of which is to be sterilized. It contains at two opposite long edges a number of slotted holes 57 which are intended for the lateral insertion of holding rods 18a and 18b. The rods 18a and 18b are provided with enlargements 29A, 29B at their ends. The enlargements 29A and 29B are shaped conically; they are used as contact surfaces. They support the shielding arrangement after being hung into the holes 57. A central hole 54 serves for inserting a rod shaped UV radiator (not shown) and its electrical leads into the shielding arrangement. The UV radiator is held centered within the shielding arrangement by means, not shown, in such a manner that its longitudinal or rod axis 13 is aligned vertically in the operations room. To this end, the UV radiator can also be fastened at the base plate 6.

The shielding arrangement consisting of two subassemblies is shown in FIG. 12 separated from the base plate 6. The shielding arrangement comprises as an essential part a major number of aperture disks 12, which each have a central circular hole 14 which has at least the diameter of the UV radiator. Each aperture disk 12 consists of a first subdisk 12A and a second subdisk 12B, which lie parallel in horizontal planes slightly displaced from each other. The subdisks 12A and 12B of each subassembly are approximately semicircular; they all have the same mutual spacing.

The individual subdisks 12A and 12B of each subassembly are held parallel to each other at some spacing. In detail, first and second holding devices are used for this purpose.

The first holding device insures that the first group of subdisks 12A is held stacked parallel and coincident with each other. Tubular holding rods 18A, which are brought through holes 17 in the first subdisks 12A perpendicular and are jammed and thus fastened in the holes 17 form the first holding device. The jamming can be accomplished by pulling a mandrel through the holding rods 18A. Other types of fastenings between the subdisks 12A and the holding rods 18A are also possible. The individual holding rods 18A have at their upper ends the already mentioned enlargement 29A, which is of conical shape. It protrudes slightly above the uppermost aperture disk 12 and engages from the top with the holes 56 of the base plate 6 when in the hung position.

The design of the second holding device is quite similar. It likewise comprises a number of tubular holding rods 18B, which are brought through holes 17 in the outer zone of the second subdisks 12B and are jammed in place. The holding rods 18B are likewise provided with a conical enlargement 29B at their upper, somewhat protruding end. These enlargements 29B engage with the slotted holes 57 of the base plate 6 from the top when in the hung position.

It is seen from the design of the shielding arrangement and its subdivision into the two subassemblies, of which each comprises one of the two groups of subdisks 12A and 12B and a holding device, that the group of all first subdisks 12A can be moved relative to the group of all second subdisks 12B between a closed position enclosing the rod shaped UV radiator 2 in the holes 12 and a release position releasing the UV radiator. For, each of the two subassemblies can easily be detached from the base plate 6 by briefly raising them (i.e., shifting in the direction of the rod axis 13 and thereby lifting the enlargements 29 out of the holes 57) and subsequently pulling them laterally out of the base plate 6. Thereupon, the UV radiator is ready for cleaning or for unshielded radiation into the operations room.

It can be seen from FIGS. 12 and 13 that the two subassemblies 12A and 12B are of identical design. Each subdisk 12A and 12B has the appearance of a washer divided in two. Therefore, all the subdisks 12A and 12B can be produced with one and the same sheet metal punch, which contributes to cost savings in production.

The first subdisks 12A always have at the center of their straight, cut edge 26A an approximately semicircular cutout 23A. Similarly, the second subdisks 12B also always have a semicircular cutout 23B at the center of their straight, cut edge 26B. The two cutouts 23A and 23B of each aperture disk 12 jointly form, in the closed position shown, the hole 14 intended to bring through the UV radiator. The cut edges 26A and 26B are therefore to be considered as contact edges.

At the two cut or contact edges 26A and 26B of the subdisks 12A and 12B of each aperture disk 12, facing each other, is further provided a semicircular recess. In the closed position the two recesses form a feedthrough 15 for a tube, not shown, which contains an electrical feed cable for the lower electrode of the UV radiator.

It will be seen from FIG. 14 that the two cut edges 26A and 26B of the two subdisks 12A and 12B of each aperture disk, facing each other, are bent toward each other. This provides a locking arrangement in the closed position, which makes unintended opening more difficult. Because of the overlap, no UV light can furthermore escape from the area of the cut edges 26A, 26B from the shielding arrangement upward or downward.

In deviation from the description so far, also more than two UV radiators with the corresponding shielding arrangements can be provided for each workroom, as required. Especially in larger work rooms, several smaller UV radiators are preferred over one large one. The UV radiators together with their shielding arrangements can furthermore be used not only in work rooms such as operating rooms and pharmaceutical production rooms as well as in leisure rooms (e.g., solariums), where germ-free air and surfaces and substances kept free of germs are important. To similar advantage and with the same effectiveness, their use in agricultural operations, particularly animal farming, is also possible. The UV radiators together with the shielding arrangement can be used, for instance, in fowl fattening rooms or pig stables and be arranged above the heads of the fowl or the pigs. In agricultural applications, the stress is mainly on health maintenance and growth promotion and on increasing the productivity. These objectives can be achieved by means of the shielding arrangements according to the invention, which are easy to install and maintain even in stables and make possible operation also in a rough environment, without the danger of harming the animals by UV radiation. Especially in the field of agriculture, the advantageous property of UV light to reduce odors after extended irradiation, can be utilized by the shielding arrangement according to the invention without danger. Because of the vertical arrangement and the thermal air convection forced thereby, blowers can generally be dispensed with. This also eliminates the danger to the animals due to drafts.

What is claimed is:

1. In a shielding arrangement for a rod shaped UV radiator, comprising a plurality of shielding plates which are held parallel to each other at a predetermined spacing by a holding device, the improvement comprising:
   a. the shielding plates being aperture disks each of which has a hole of a size at least large enough for leading the UV radiator through it in the direction of its rod axis;
   b. the holes of all the individual aperture disks aligned axially with respect to each other; and
   c. the aperture disks matched to each other with respect to their hole dimension (2r), their outside dimension (2R), their thickness (d) and their mutual spacing (a) in such a manner that UV light which emanates from a section of the UV radiator located between two adjacent aperture disks when the UV radiator is placed axially through the aligned holes issues with a small aperture angle ($\alpha$) essentially only between these two adjacent aperture disks but not between other aperture disks.

2. A shielding arrangement according to claim 1 wherein the holes of the aperture disks are made slightly larger than the outside diameter (2p) of the rod shaped UV radiator.

3. A shielding arrangement according to claim 2, wherein the difference between the hole diameter (2r) and the outside diameter (2p) of the UV radiator is between 1 cm and 4 cm.

4. A shielding arrangement according to claim 1 wherein the thickness (d) of the aperture disks is substantially smaller than their outside dimension.

5. A shielding arrangement according to claim 1 wherein said aperture disks are circular and are arranged concentrically to each other.

6. A shielding arrangement according to claim 1 wherein all aperture disks have the same outside dimensions (2R).

7. A shielding arrangement according to claim 1 wherein the aperture disks which follow each other in the connecting line of the holes have increasing outside dimensions.

8. A shielding arrangement according to claim 1 wherein the mutual spacing of all aperture disks is the same.

9. A shielding arrangement according to claim 1 wherein the spacings of an aperture disk from its adjacent aperture disks are different.

10. A shielding arrangement according to claim 9 wherein the aperture disks which follow each other in the connecting line of the holes have increasing outside dimensions and the mutual spacing of the aperture disks becomes smaller with decreasing outside dimension of the aperture disks.

11. A shielding arrangement according to claim 1 wherein the aperture disks are flat.

12. A shielding arrangement according to claim 1 wherein the aperture angle ($\alpha$) of the UV light issuing between two adjacent aperture disks is smaller than 20°.

13. A shielding arrangement according to claim 12 wherein the ratio of the spacing ($a$) of two adjacent aperture disks to one-half the outside dimension (R) of one of said two aperture disks is smaller than 0.35 and the ratio of the hole dimension (2r) to the outside dimension (2R) of one of said aperture disks is smaller than 0.33.

14. A shielding arrangement according to claim 1 wherein the aperture disks are made, at least partially, of a UV resistant plastic material.

15. A shielding arrangement according to claim 1 wherein the aperture disks are provided with a layer highly reflective to UV light at least on one side.

16. A shielding arrangement according to claim 15 wherein the reflecting layer consists of aluminum.

17. A shielding arrangement according to claim 1 wherein the aperture disks consist, at least in part, of metal.

18. A shielding arrangement according to claim 17 wherein the aperture disks consist completely of aluminum.

19. A shielding arrangement according to claim 1 wherein the aperture disks have a layer which is highly absorbant to UV light on one side.

20. A shielding arrangement according to claim 19 wherein said absorbing layer is mat black varnish.

21. A shielding arrangement according to claim 1 wherein said holding device comprises at least three holding rods which are brought through holes in the aperture disks and respective spacers through which a hole is drilled placed between each two adjacent aperture disks.

22. A shielding arrangement according to claim 21 wherein said spacers are of cylindrical design.

23. A shielding arrangement according to claim 21 wherein the aperture disks and the spacers are detachably clamped together at the holding rods by means of a clamping device.

24. A shielding arrangement according to claim 1 wherein said holding device together with said aperture disks forms a removable and transportable structural unit.

25. A shielding arrangement according to claim 24 wherein the aperture disks have a slot which leads to their central hole for inserting the UV radiator.

26. A shielding arrangement according to claim 1 and further including a vertical support member for holding the aperture disks substantially horizontal in the operations room to be irradiated.

27. A shielding arrangement according to claim 26 wherein said holding device is detachably fastened to said vertical support member.

28. A shielding arrangement according to claim 27 wherein said holding device is detachably fastened to said vertical support member by at least one holding tube.

29. A shielding arrangement according to claim 28 wherein a supply cable for the electrode of the UV radiator is run in said holding tube.

30. A shielding arrangement according to claim 28 wherein said vertical support member comprises holding plates, which are wider than the slots in the aperture disks, fastened to said holding tube.

31. A shielding arrangement according to claim 26 wherein said holding device is connected to said vertical support member through a ballast box which contains the components necessary for the electrical operation of the UV radiator.

32. A shielding arrangement according to claim 31 wherein one socket for the UV radiator is arranged at the ballast box.

33. A shielding arrangement according to claim 32 wherein the other socket of the UV radiator is attached to said holding tube.

34. A shielding arrangement according to claim 1 wherein the hole of the aperture disk which is located at one of the two outer ends of the arrangement is covered up by a socket of the UV radiator which is on the outside.

35. A shielding arrangement according to claim 1 wherein said aperture disks are used as the electrodes of an electric high voltage insect trap.

36. A shielding arrangement according to claim 35 where adjacent aperture disks are at different electric potentials.

37. A shielding arrangement according to claim 1 and further including a suspension device for the purpose of suspending it from the ceiling of the operations room.

38. A shielding arrangement according to claim 1 and further including a mounting device for the purpose of installing said arrangement on the floor of the operations room.

39. A shielding arrangement according to claim 38 wherein said mounting device is movable.

40. A shielding arrangement according to claim 1 wherein:
 a. each aperture disks comprises a first and a second subdisk;
 b. the group of all first subdisks is arranged joined with the group of all second subdisks to provide a closed position enclosing the UV radiator within said holes; and
 c. means for releasing at least one of the groups from the closed position, into a release position releasing the UV radiator.

41. A shielding arrangement according to claim 40 wherein said first subdisks have an essentially semicircular cutout at their edges and are held in parallel relationship in a coincident stack by means of a first holding device; said second subdisks have an essentially semicircular cutout at their edges and are held parallel to each other in a coincident stack arrangement by means of a second holding device which is independent of said first holding device; and wherein at least the group of all first subdisks are movable relative to the group of all second subdisks in such a manner that, in the closed position, the two subdisks belonging to an aperture disk lie substantially in the same plane and their curouts then jointly form said hole for the insertion of the UV radiator, and that, in the release position, the first subdisks are moved away from the second subdisks, exposing at least partially the UV radiator.

42. A shielding arrangement according to claim 40 wherein the contact edges of the two subdisks of each aperture disk facing each other are bent toward each other out of the plane of the disk, so that they engage each other in the form of a locking arrangement in the closed position.

43. A shielding arrangement according to claim 40 wherein the two subdisks of an aperture disk have the same external shape.

44. Shielding arrangement according to claim 40 wherein the holding device of at least one of the groups of subdisks consists of tubular holding rods passing through holes in the subdisks and jammed in said holes.

45. A shielding arrangement according to claim 44 wherein said holding rods have enlargements on one of their ends for engagement with holes in a base plate.

* * * * *